United States Patent [19]
Hasson

[11] Patent Number: 5,580,344
[45] Date of Patent: Dec. 3, 1996

[54] INCISION CONVERTER & METHOD OF USING THE SAME

[76] Inventor: Harrith M. Hasson, 2043 N. Sedgwick, Chicago, Ill. 60614

[21] Appl. No.: 396,892

[22] Filed: Mar. 1, 1995

Related U.S. Application Data

[63] Continuation of Ser. No. 964,915, Oct. 22, 1992, abandoned.
[51] Int. Cl.⁶ ................................................. A61B 17/00
[52] U.S. Cl. ........................ 600/219; 600/201; 600/210; 600/215; 600/216; 600/217; 604/104; 604/106
[58] Field of Search ................................. 600/201, 210, 600/214, 215, 216, 217, 219; 604/104, 105, 106, 160, 161, 164

[56] References Cited

U.S. PATENT DOCUMENTS

| | | | |
|---|---|---|---|
| 530,728 | 12/1894 | Sherbrook | 606/198 |
| 3,965,890 | 6/1976 | Gauthier | 128/20 |
| 4,716,901 | 1/1988 | Jackson et al. | 604/160 |
| 5,002,557 | 3/1991 | Hasson | 604/42 |
| 5,176,687 | 1/1993 | Hasson et al. | 606/127 |

Primary Examiner—Corrine M. McDermott
Assistant Examiner—N. Kent Gring
Attorney, Agent, or Firm—Wood, Phillips, VanSanten, Clark & Mortimer

[57] ABSTRACT

A guide for a cannula extending through a tissue and into a cavity in which a surgical procedure is to be performed. The guide has first and second plates cooperatively defining a through passageway for a cannula. Structure connects between the first and second plates to allow selective altering of the relative positions of the first and second plates to thereby change the configuration of the through passageway defined cooperatively between the first and second plates. A conversion unit can be used to draw the plates away from each other to enlarge an incision into which the first and second plates extend.

28 Claims, 3 Drawing Sheets

INCISION CONVERTER & METHOD OF USING THE SAME

This application is a continuation of application Ser. No. 07/964,915, filed Oct. 22, 1992 now abandoned.

BACKGROUND OF THE INVENTION

1. Field of the Invention

This invention relates to internal surgery and, more particularly, to structure for conversion of an incision from a laparoscopic incision to a mini-laparotomy incision. The invention further contemplates a surgical procedure using the above structure.

2. Background Art

Laparoscopy is now a widely used surgical procedure. In laparoscopy, a cannula is directed through tissue to access an internal cavity. The cannula has a relatively small diameter which requires only a small incision in the tissue.

In some procedures, numerous cannulae are simultaneously used. Different types of instruments can be directed through the cannulae for simultaneous use, including a camera that allows monitoring of the procedure at a remote location. The inventor herein has invented a number of instruments to be used to perform various laparoscopic procedures, some of which are separately patented.

Laparoscopy has several advantages over conventional surgery. Most significantly, it allows the performance of surgery on an out-patient basis. This is made possible by the fact that the procedure generally only requires a small incision at each point of entry.

One drawback with laparoscopy is that while the small incisions promote early recovery, they do not lend themselves to the removal of large objects from within the cavity. While it is possible to morsel the organs or other matter in situ, in many cases this is not practical or safe. Morselling a cancerous growth or infected material may expose the internal organs to cancerous cells or infected matter.

In those instances when it is anticipated that a large object will be removed from within a cavity, it has heretofore been the general practice to perform conventional surgery even though the only requirement for the larger incision is the removal of the matter from within the cavity. The result is a lengthened hospitalization period and significant discomfort to the person on whom the operation is performed.

SUMMARY OF THE INVENTION

The present invention is specifically directed to overcoming the above-enumerated problems in a novel and simple manner.

More particularly, in one form, the invention contemplates a guide for a cannula extending through a tissue and into a cavity in which a surgical procedure is to be performed. The guide has first and second plates cooperatively defining a through passageway for a cannula. Structure connects between the first and second plates to allow selective altering of the relative positions of the first and second plates to thereby change the configuration of the through passageway defined cooperatively between the first and second plates.

In one form, the first and second plates are completely separable, each from the other, and the structure connecting the first and second plates is a cap that surrounds the first and second plates. The cap can have an adjusting screw, or the like, extending therethrough and against at least one of the first and second plates so that turning of the screw moves the plates relative to each other.

The invention also contemplates structure for urging the first and second plates apart from each other with the first and second plates extending through an incision so that the plates urge tissue surrounding the incision oppositely to enlarge the size thereof.

In one form, a ring is provided to be placed on the tissue. Structure is provided to draw the first and second plates oppositely to each other utilizing the ring as a support.

In one form, the structure used to draw the plates away from each other is at least two elongate elements each having an alterable length. The length of the elements can be changed in a number of ways. With one exemplary structure, first and second relatively movable parts are provided and with the first and second parts in different positions different effective lengths for the elongate elements result. In one form, the first and second parts are telescopingly engaged, one with the other, and normally biased to a lengthened state. A ratchet mechanism can be used to releasably hold the first and second parts in a plurality of different positions.

The elongate elements can be releasably connected to the plates for convenience of assembly and disassembly and are adjustable relative to the ring for further versatility. In one form, a cooperating hook and loop combination is provided with one each on the elongate elements and plates.

To stabilize the plates and facilitate enlargement of an incision, a guide plate can be provided on at least one of the first and second plates. The guide plate is extendable to increase the effective length of the first and second plates to provide extension of the subassembly, made up of the first and second and guide plates, fully through tissue, regardless of its thickness. A separate key element can be provided to reposition the guide plate(s) relative to the first and second plates. Alternatively, a movable guide sleeve can be used that fully surrounds the first and second plates.

The invention further contemplates an apparatus for selectively enlarging the size of an incision, which apparatus has a ring for placement against a tissue through which an incision is made, first and second plates to be extended into an incision, and structure cooperating between each of the first and second plates and the ring at diametrically opposite locations thereon for drawing the first and second plates away from each other to enlarge the size of the incision into which the first and second plates extend.

The invention further contemplates a method of enlarging an incision in a tissue, which method includes the steps of placing a ring on the tissue so that the ring surrounds the incision, placing first and second plates into the incision, and drawing the plates towards diametrically opposite locations on the ring to thereby enlarge the diameter of the incision.

The first and second plates can be held together in a predetermined relationship with there being a passageway defined therebetween for receiving a cannula. The cannula can be removed at the time that the incision is to be enlarged.

The invention further contemplates the step of placing a guide plate or sleeve on at least one of the first and second plates and using the guide plate(s) to assist direction of the first and second plates through an incision and stabilize the plates as the incision is enlarged.

The invention further contemplates the step of surrounding the first and second plates with a cap to hold the first and second plates together in assembled relationship with a cannula passageway being defined between the first and second plates. The cap can be used to alter the relative positions of the first and second plates to selectively lock and release the cannula to permit movement thereof.

The first and second plates can also be used to captively hold a tissue to maintain a cannula in an operative position. In one form, a cannula with an inflatable membrane is employed with the membrane being selectively placed in expanded and collapsed states. The cannula can be directed through the passageway with the membrane collapsed and thereafter the membrane can be expanded to define a blocking shoulder. The cannula can be drawn up to seat the shoulder on the inside of the tissue whereupon the plates can be pressed down into the tissue to captively hold the tissue.

Once the procedure using the cannula is completed, the cannula can be removed and the first and second plates drawn away from each other to enlarge the incision. The first and second plates can be subsequently removed and replaced with a number of conventional retractor elements to maintain the incision open and readily accessible to the surgeon.

The invention further contemplates a method of performing surgery including the steps of directing a cannula through an incision in tissue so that the cannula extends into a cavity in which surgery is to be performed, holding the cannula in an operative position relative to the tissue, performing a procedure in the cavity using the cannula, placing a converter unit on the cannula, and using the converter unit to enlarge the incision.

According to the invention, the surgeon can perform a laparoscopic surgical procedure, at the completion of which the cannula-receiving incision can be enlarged sufficiently to remove a growth, or the like, intact from the cavity. In the case of a very large, solid tumor, the tumor can be externalized and morselled outside the abdomen without endangering the organs inside the abdominal cavity. A large cystic tumor likewise can be decompressed outside the abdomen after being externalized, thereby avoiding contamination or spillage into the abdominal cavity. The incision need not be made as large as would be required to carry out a conventional surgical procedure. Furthermore, the recovery time for the patient would be similar to that with laparoscopy and less than would be required with a conventional procedure. This is because only laparoscopic manipulations are carried out inside the abdomen.

Once the incision is enlarged, the converter unit can be disassembled and the retracting elements can be substituted therefor. An object can then be removed from the body cavity through the enlarged incision which is subsequently closed by conventional techniques.

DETAILED DESCRIPTION OF THE DRAWINGS

Figure 6:
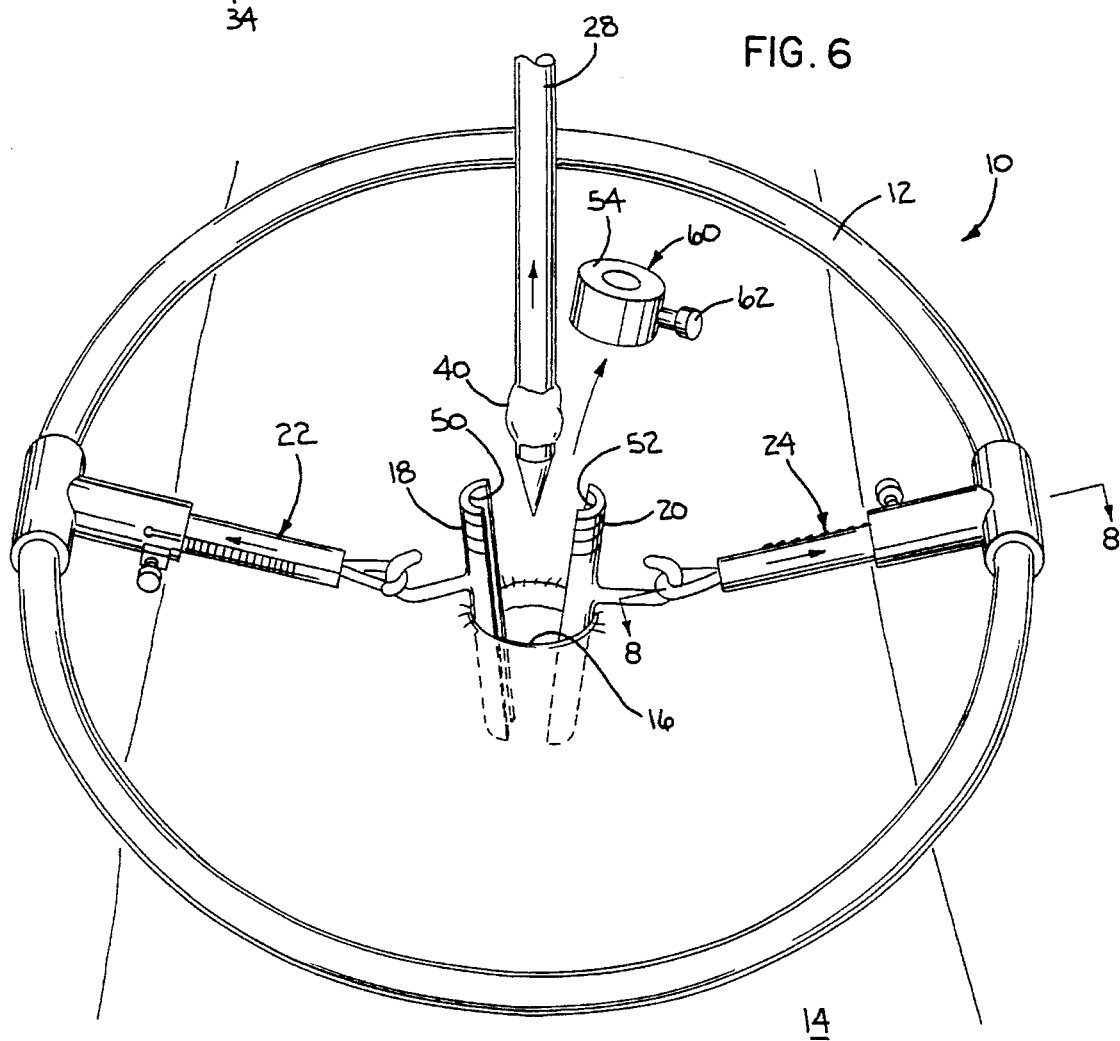
FIG. 6 is a perspective view of the converter unit further including a ring and structure for drawing the plates away from each other and with the cannula removed and the plates drawn away from each other to enlarge the incision.

Referring initially to FIG. 6, an incision converter unit, according to the present invention, is shown at 10. The converter unit 10 consists of a ring 12 for placement against a tissue 14 in surrounding relationship to an incision 16. The ring 12 is used as a brace to draw first and second plates 18, 20, extending through the incision 16, away from each other to thereby enlarge the diameter of the incision 16 through which the plates 18, 20 extend. Drawing means 22, 24 cooperate between the plates 18, 20 and the ring 12. The drawing means 22, 24 are each in the form of an elongate element, the length of which can be selectively diminished to draw the plates 18, 20 away from each other to enlarge the size of the incision 16.

Figure 4:
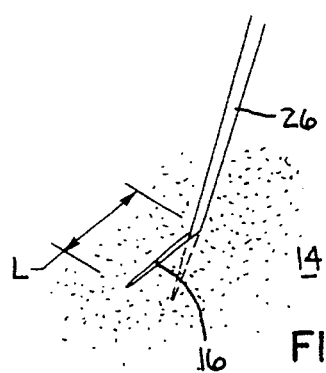
FIG. 4 is a perspective view of a body tissue showing the step of creating an incision therein at the initiation of a surgical procedure.

The structure of the inventive converter unit 10 will be described in detail as its function is described step-wise through the performance of a surgical procedure. The surgical procedure is initiated by making the incision 16 in the tissue 14 utilizing a conventional scalpel 26, as seen in FIG. 4. The length L of the incision 16 is chosen to accommodate a conventional laparoscopic cannula 28, typically having a 10 to 11 mm outside diameter. The plates 18, 20 are preferably made from plastic having a thickness of on the order of 7 mm. Thus, the diameter of the cannula 28, with the plates 18, 20 thereon, is approximately 25 mm. While the initial incision is usually made only slightly larger than the diameter of the cannula 28, i.e., on the order of 13–14 mm, it will ultimately be cut, as described below, to accommodate the plates 18, 20.

The cooperation between the converter unit 10 and cannula 28 is shown most clearly in FIGS. 1–6. The cannula 28 has an internal passageway 30 through which instruments (not shown) can be directed. The cannula 28 is guided through the incision 16 by a trocar 32 with a sharpened end 34 that is directed fully through the cannula passageway 30 to be exposed beyond the leading end 36 of the cannula 28. The sharpened end 34 wedges the tissue 14 around the incision 16 apart to permit smooth entry of the cannula 28. Once the leading end 36 of the cannula 28 passes fully through the tissue 14 and into the body cavity 38, in which a procedure is to be performed, the trocar 32 is withdrawn.

The cannula 28 extends sufficiently through the tissue 14 that a flexible membrane 40 thereon resides fully within the cavity 38. The membrane 40 can be placed selectively in a collapsed state, as shown in FIG. 6, and an expanded state, shown in FIGS. 1, 3 and 5. In the collapsed state for the membrane 40, the membrane 40 closely embraces the outer surface 42 of the cannula 28 so as not to obstruct the smooth passage of the cannula 28 through the tissue 14. Once expanded, the membrane 40 defines an annular shoulder 44 which can be drawn upwardly against the inside surface 46 of the tissue to both seal around the incision 16 and prevent withdrawal of the cannula 28. The membrane 40 is selectively expanded and collapsed through an external control 48. The details of a suitable control 48 and membrane 40 are fully explained in my U.S. Pat. No. 5,002,557.

Once the cannula 28 is fully inserted and the membrane 40 expanded, the plates 18, 20 can be assembled to the cannula 28. The plate 18 has a curved surface 50 and the plate 20 a curved surface 52 which cooperatively define a receptacle/passageway 53 for the cannula 28. A cap 54 surrounds the upper ends 56, 58 of the plates 18, 20 to maintain the same in an operative relationship so as to define the passageway 53. The cap is preassembled to the cannula and is slidable selectively therealong to engage, and disengage from, the plates 18, 20. The configuration of the passageway 53 i.e. the diameter, can be altered by providing an adjusting means 60 on the cap 54. The adjusting means 60 has a set screw 62 threaded through one wall 64 of the cap 54 so as to bear against the plate 20. By tightening the set screw 62, the end 66 of the screw 62 bears on the plate 22 which draws the opposite wall 68 of the cap 54 more positively against the cannula 28 to thereby lock the plates 18, 20 in a desired position relative to the cannula 28. With this arrangement, the plates 18, 20 and cap 54 can be preassembled with the cap 54 loosely engaging the plates 18, 20 to allow the plates 18, 20 and cap 54 to slide as a unit relative to the cannula 28 at the initiation of the surgery.

Figure 3:
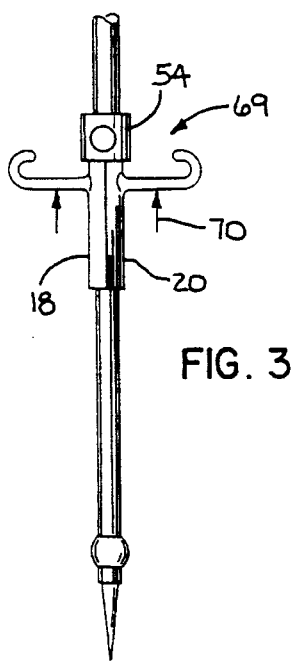
FIG. 3 is a side elevation view of the converter unit slid upwardly on a cooperating cannula to a position to allow initiation of a laparoscopic surgical procedure.
Figure 5:
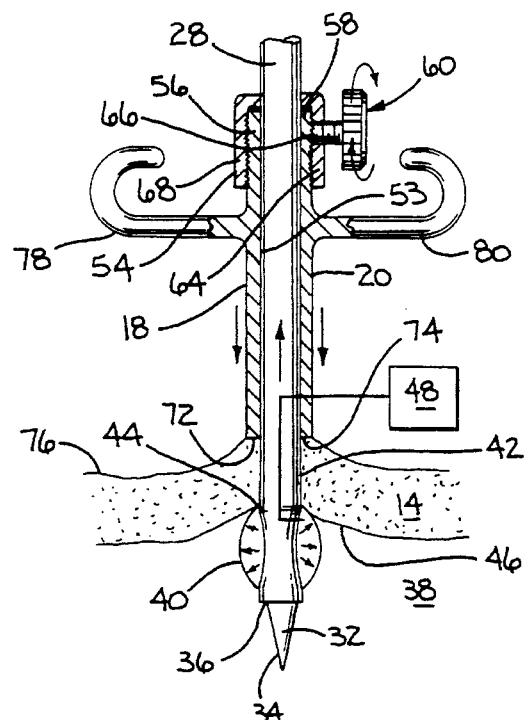
FIG. 5 is a side elevation view showing the converter unit holding the cannula in operative position relative to a tissue through which the cannula extends.

To perform a laparoscopic surgical procedure with the converter unit 10, the plates 18, 20 with the cap 54 thereon, which together define a subassembly 69, are retracted in the direction of arrows 70 in FIG. 3. Once the cannula 28 is inserted and the membrane 40 expanded, the cannula 28 is drawn upwardly to seat the shoulder 44 against the tissue 14. The plates 18, 20 are then slid downwardly as a unit until the lower edges 72, 74 thereon bear on the outer surface 76 of the tissue 14, as shown in FIG. 5. The cannula 28 is thus supported by the tissue 14 which is captively held between the plates 18, 20 and the membrane 40. The set screw 62 can be tightened to fix the positions of the plates 18, 20. A laparoscopic procedure can then be carried out through the cannula 28.

Once the laparoscopic excision of an abdominal mass, tumor or cyst or other laparoscopic procedure is completed, the incision can be enlarged to convert it to a mini-laparotomy incision as to allow removal of objects from within the body cavity 38. To accomplish this, according to the invention, the ring 12 is placed on the tissue 14 in surrounding relationship to the cannula with the subassembly 69 thereon.

The ring 12 is preferably made from metal with a diameter that is chosen depending upon the desired size of the incision, i.e. a larger diameter ring 12 can produce a larger incision opening. It should be noted that while a ring 12 is described, other different configurations for the "ring" 12 would be usable according to the invention so long as they afford diametrically opposite bracing surfaces.

Figure 1:
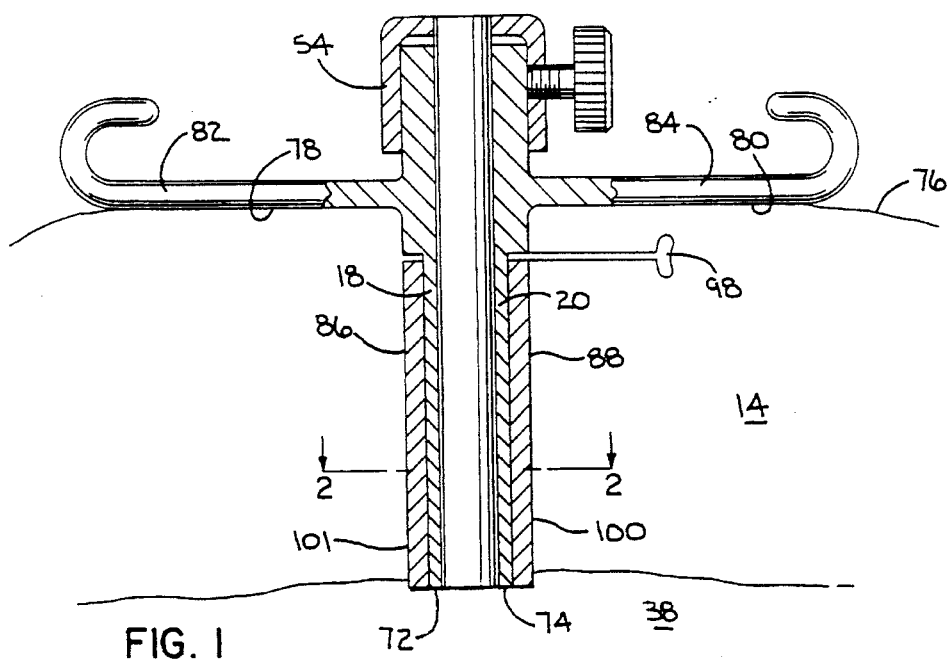
FIG. 1 is a cross-sectional, side elevation view of an incision converter unit according to the present invention, including first and second plates.
Figure 2:
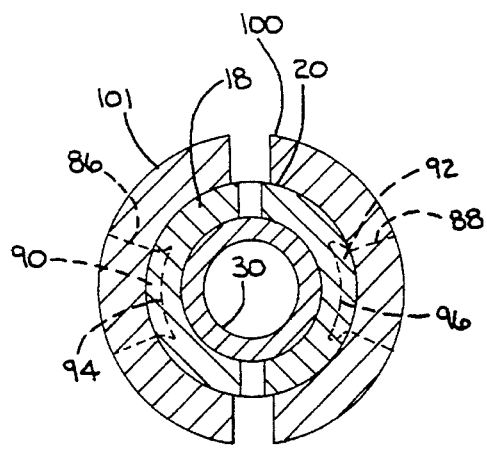
FIG. 2 is a cross-sectional view of the converter unit taken along line 2—2 of FIG. 1.

The set screw 62 is loosened to allow retraction of the subassembly 69, as shown in FIG. 3. This exposes the incision, which can then be cut to the desired length. The fascia can then be exposed using conventional S-type retractors and cut to the same size. Once the incision 16 is enlarged, the subassembly 69 is pushed down so that the plates 18, 20 move through the incision 16 until the bottom edges 78, 80 of hooks 82, 84, on the plates 18, 20, abut the outer surface 76 of the tissue 14, as seen in FIG. 1. Preferably, the edges 72, 74 project fully through the tissue 14 to be exposed in the cavity 38 to stabilize the subassembly 69 as the incision is enlarged.

To accommodate tissues 14 that are thicker than the distance between the edges 78, 80 and 72, 74, guide plates 86, 88 are provided. The guide plates 86, 88, which are preferably made from metal or hard plastic, have flanges 90, 92 movable within slots 94, 96 in the plates 18, 20 guidingly in a longitudinal direction relative to the plates 18, 20. By moving the guide plates 86, 88 downwardly in FIG. 1 relative to the plates 18, 20, the effective length of the subassembly 69 can be increased to allow it to extend fully through the tissue 14, which is important for reasons that will be made apparent from the description below. A separate key element 98 can be used to wedge the guide plates 86, 88 downwardly relative to the plates 18, 20.

In an alternative form, guide sleeves 100 and 101 extend around the plates 18, 20 and are movable lengthwise relative thereto. The key element 98 can be used to slide the guide sleeves 100, 101 in the same manner as it is used to reposition the guide plates 86, 88.

Typically, the plates 18, 20 may have a length on the order of 6 cm. The guide plates 86, 88 permit a lengthening of 3 cm to 9 cm total. Similarly, plates 18, 20 with a 10 cm length could be extended to 15 cm.

As an alternative to using the guide plates 86, 88 and guide sleeves 100, 101, longer first and second plates 18, 20 can be substituted. However, the shorter plates 18, 20 are used more universally. If the plates 18, 20 are too long, insertion thereof may be limited.

Once the subassembly 69 is situated as in FIG. 1, the cap 54 is removed to allow the plates 18, 20 to separate, each from the other. The drawing means 22, 24 are then used to pull the plates 18, 20 away from each other to enlarge the size of the incision 16. The details of the drawing means 22, 24 are shown in FIGS. 6–10.

One exemplary drawing means 24 is described. Each of the drawing means 22, 24 is substantially the same. While any number of drawing means 22, 24 can be used, two such drawing means, 22, 24 are described for purposes of illustration. Typically, four or five of such drawing means 22, 24 would be employed.

The drawing means 24 is an elongate element having first and second cooperating parts 102, 104. The first part 102 has a T-shaped configuration with a stem 106 and a cross bar 108. The cross bar 108 is hollow and slightly curved to accept the ring 12 and be slidable circumferentially therealong. A set screw 110 allows the cross-bar 108 to be fixed at a desired location relative to the ring 12.

The second part 104 is telescoped within the stem 106 of the first part 102. A coil spring 112 acts between the ring 12 and end 114 of the part 104 to urge the part 104 away from the ring 12 to tend to lengthen the drawing means 24.

At the end 116 remote from the ring 12 a loop 118 is provided for releasably connecting to one of the hooks 82, 84 on the plates 18, 20. The loop 118 can be conveniently placed over the hooks 82, 84. A releasable arm 120 can be deformed to snap-fit the hook 118 in place. Alternatively, a one piece, closed loop can be used at the end 116.

Figure 8:
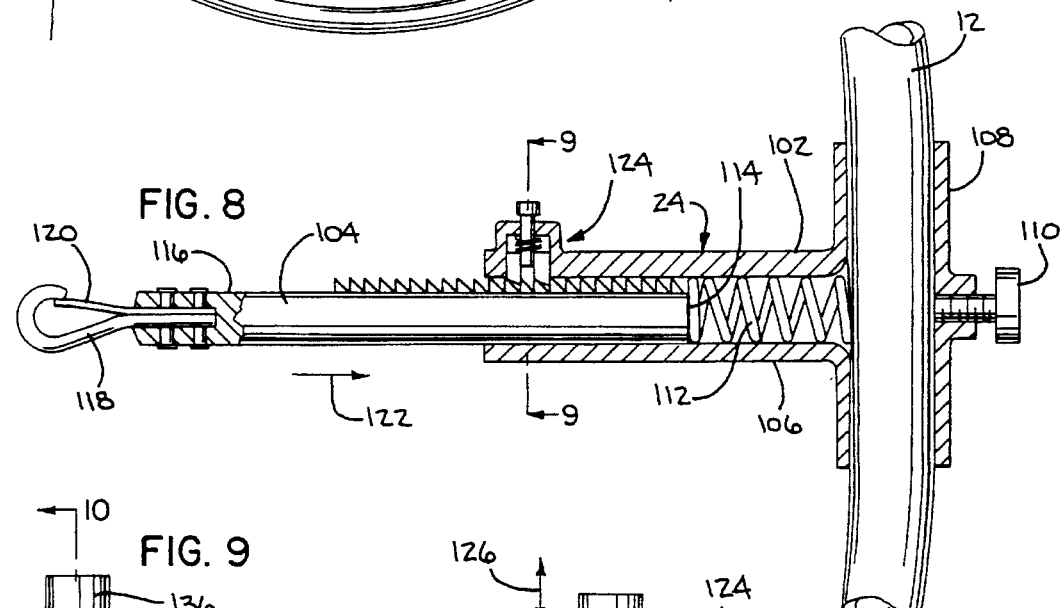
FIG. 8 is an enlarged, cross-sectional view of one of the elements for drawing the plates towards the ring to thereby enlarge an incision.
Figure 9:
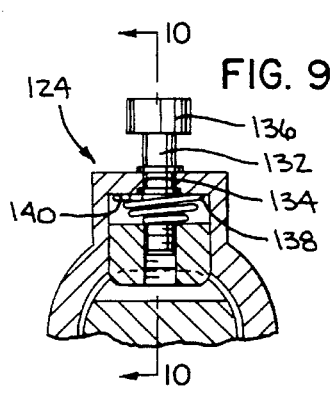
FIG. 9 is a cross-sectional view of a ratchet mechanism for holding two separate parts on each drawing element in different relative positions and taken along line 9—9 of FIG. 8.
Figure 10:
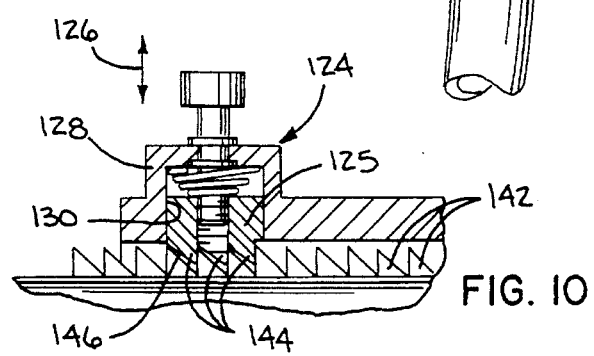
FIG. 10 is a cross-sectional view of the ratchet mechanism taken along line 10—10 of FIG. 9.

With the loop 118 connected to one of the hooks 82, 84, the length of the drawing means 24 can be diminished by urging the part 104 from left to right in FIG. 8, in the direction of the arrow 122, against the force of the spring 112. This draws the plate 20 towards the ring 12 to thereby enlarge the size of the incision 16.

A ratchet means is provided at 124 to maintain the first and second parts 102, 104 in a plurality of different positions corresponding to different lengths for the drawing means 24. The ratchet means 124 has a toothed block 125 guided in a translatory path towards and away from the second part 104 in the direction of double-headed arrow 126. An enlarged portion 128 on the stem 106 defines an internal guide surface 130 for the block 125.

The block 125 is carried by a post 132 which extends through a bore 134 in the enlarged portion 128 to be guided in the line of the double-headed arrow 126. The post 132 has an exposed, enlarged head 136 to facilitate its repositioning. A spring 138 acts between a shoulder 140 on the enlarged portion 128 and the block 125 to normally urge the block 125 against the second part 124.

The second part 104 has a plurality of teeth 142 to mesh with teeth 144 on the block 125. The teeth 144 have cam edges 146 which are wedged by the teeth 142 radially outwardly as the second part 104 is moved from left to right in FIGS. 8 and 10. As the second part 104 is moved from left to right, the block 125 is repeatedly cammed upwardly by the teeth 142 and downwardly by the spring 138 as the teeth 142, 144 cross.

With the ring 12 in place and the drawing means 22, 24 operatively connected to the plates 18, 20, the second part 104 on each of the drawing means 22, 24 can be manually pulled outwardly towards the ring 12. The ratchet mechanism 124 holds the drawing means 22, 24 in the shortened state. The drawing means 22, 24 can be operated at the same time to prevent shifting of the ring 12 relative to the incision 16. The drawing means 22, 24 can be released to their extended state by drawing upwardly on the head 136 of the post 132 to disengage the block 125 from the teeth 142 on the second part 104. The spring 112 then biases the second part 104 to its extended state which relaxes the pressure on the plates 18, 20.

Figure 7:
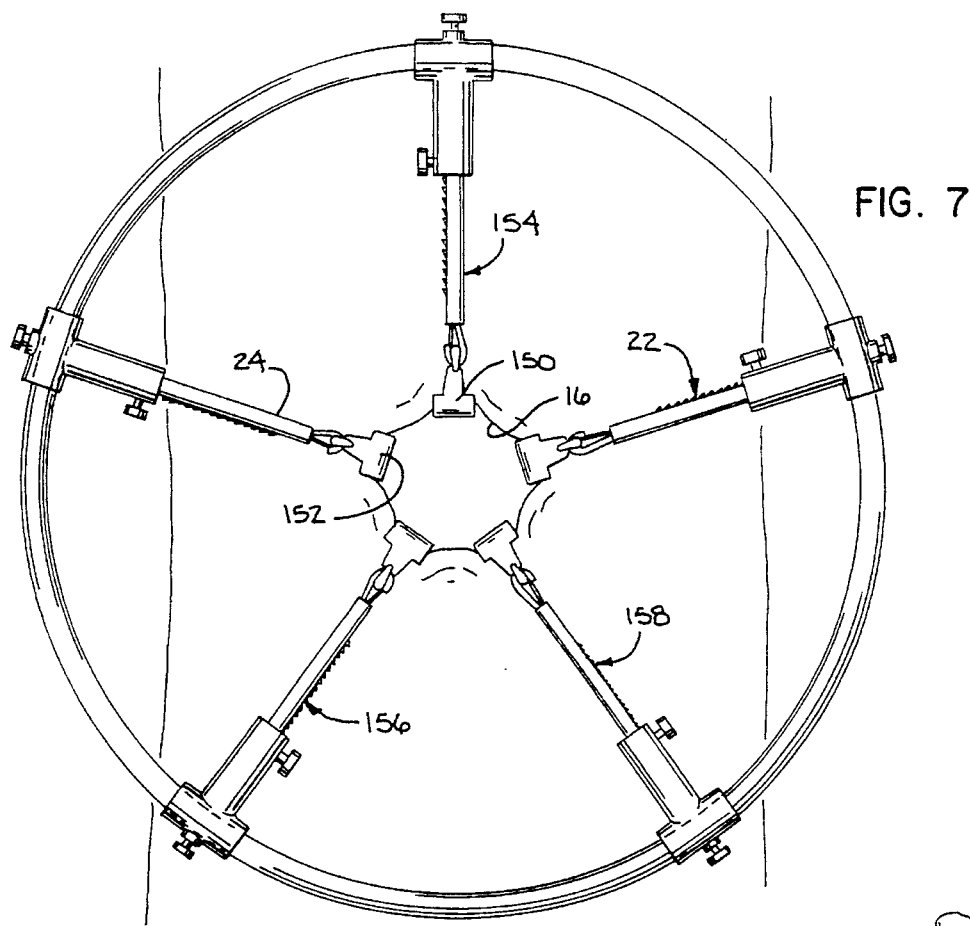
FIG. 7 is a plan view of an incision fully enlarged with the converter unit according to the present invention and with conventional retracting elements substituted for the first and second plates.

Once the size of the incision is enlarged sufficiently to accommodate conventional retractor elements 150, the plates 18, 20 can be replaced with the conventional retractor elements 150, as shown in FIG. 7. The retractor elements 150 have hooked ends 152 to engage the loop 118 of the drawing means 24. The retractor plates 18, 20 can be replaced one by one with the retractor elements 150.

Once the incision 16 is enlarged as in FIG. 7 and held open by the retractor elements 150, the desired procedure can be carried out. Typically, this involves the removal of tissues or organs detached from their anatomical sites by laparoscopic means or the performance of delicate microsurgical procedures on tissues or organs externalized by this instrument and method following appropriate laparoscopic manipulation (with or without laparoscopic dissection). The removal of objects can be done with or without a protective pouch, as disclosed in my co-pending application Ser. No. 698,567.

Once the procedure is completed, the drawing means 22, 24, and the additional drawing means 154, 156, 158, shown in FIG. 7, can be released in sequence to allow the entire converter unit 10 to be withdrawn from the site. The fascia is then closed with sutures. Reinsufflation of the abdomen can then be carried out for final lavage and inspection.

The foregoing disclosure of specific embodiments is intended to be illustrative of the broad concepts comprehended by the invention.

I claim:

1. In combination, a guide for a cannula extending through a tissue and into a cavity in which a surgical procedure is to be performed, said cannula guide comprising:

first and second plates cooperatively defining a through passageway for guidingly receiving a cannula;

means cooperating between the first and second plates for selectively altering the relative positions of the first and second plates to thereby change the configuration of the through passageway defined cooperatively between the first and second plates; and means for urging the first and second plates apart from each other with the first and second plates extended through an incision in tissue so that the plates urge tissue surrounding an incision oppositely to enlarge the size of an incision through which the first and second plates extend, said urging means comprising a ring separate from the means cooperating between the first and second plates for placement on tissue around an incision and first and second means cooperating between the ring and the first and second plates for drawing the first and second plates oppositely away from each other to enlarge an incision into which the first and second plates extend.

2. The cannula guide according to claim 1 wherein the first and second plates are completely separable, each from the other.

3. The cannula guide according to claim 1 wherein the cooperating means comprises means for surrounding the first and second plates.

4. The cannula guide according to claim 3 wherein the cooperating means further includes adjustment means extending through the surrounding means and against at least one of the first and second plates.

5. The cannula guide according to claim 1 wherein the first and second drawing means connect one each between the first and second plates and the ring, each said first and second drawing means comprising an elongate element and including means for selectively altering the length of the elongate elements.

6. The cannula guide according to claim 5 wherein each elongate element includes first and second relatively movable parts with there being releasable ratchet means cooperating between the first and second relatively movable parts to maintain the first and second relatively movable parts in a plurality of different positions, said elongate elements having different effective lengths with the first and second relatively movable parts in each of said plurality of different positions.

7. The cannula guide according to claim 1 wherein there are means cooperating between the drawing means and ring for changing the relative position of the drawing means and ring.

8. The cannula guide according to claim 1, wherein there are means cooperating between at least one of the first and second drawing means and one of the first and second plates for releasably connecting the one of the first and second drawing means and the one of the first and second plates.

9. A guide for a cannula extending through tissue and into a cavity in which a surgical procedure is to be performed, said cannula guide comprising:

first and second plates cooperatively defining a through passageway for a cannula;

means cooperating between the first and second plates for selectively altering the relative positions of the first and second plates to thereby change the configuration of the through passageway defined cooperatively between the first and second plate; and a guide plate movable lengthwise relative to the first and second plates.

10. The cannula guide according to claim 9 in combination with a key element for repositioning the guide plate in a lengthwise direction relative to the first and second plates.

11. An apparatus for selectively enlarging the size of an incision, said apparatus comprising:

a ring for placement against a tissue through which an incision is made;

first and second plates cooperatively defining a through passageway having a length for a cannula, said plates being extendable into an incision to be enlarged;

a guide plate movable lengthwise relative to the first and second plates; and means cooperating between each of the first and second plates and the ring at diametrically opposite locations thereon for drawing the first and second plates away from each other to enlarge the size of the incision into which the first and second plates extend.

12. The incision enlarging apparatus according to claim 11 including means cooperating between the ring and first and second drawing means for changing the relative positions of the first and second drawing means and the ring.

13. The incision enlarging apparatus according to claim 11 including means for releasably connecting each of the first and second drawing means to the first and second plates.

14. The incision enlarging apparatus according to claim 11 wherein at least one of the drawing means comprises an elongate element made up of first and second relatively movable parts with there being means for releasably maintaining the first and second parts in a plurality of different positions, said elongate element having a different effective length with the first and second relatively movable parts in each of said plurality of different positions.

15. The incision enlarging apparatus according to claim 14 wherein the first and second parts are telescopingly engaged, one within the other.

16. The incision enlarging apparatus according to claim 15 including means for normally biasing one of the first and second parts relative to the other of the first and second parts.

17. An apparatus for selectively enlarging the size of an incision, said apparatus comprising:

a ring for placement against tissue through which an incision is made;

first and second plates to be extended into an incision to be enlarged;

first and second means cooperating between each of the first and second plates and the ring at diametrically opposite locations thereon for drawing the first and second plates away from each other to enlarge the size of an incision into which the first and second plates extend;

means for releasably connecting each of the first and second drawing means to the first and second plates, wherein the connecting means includes a hook on one of at least one of the first and second drawing means and at least one of the first and second plates and a loop on the other of the at least one of the first and second drawing means and at least one of the first and second plates for reception of the hook.

18. An apparatus for selectively enlarging the size of an incision, said apparatus comprising:

a ring for placement against tissue through which an incision is made;

first and second plates to be extended into an incision to be enlarged;

means cooperating between each of the first and second plates and the ring at diametrically opposite locations thereon for drawing the first and second plates away from each other to enlarge the size of an incision into which the first and second plates extend; and a guide sleeve surrounding a portion of the first and second plates.

19. A method of enlarging an incision in a tissue, said method comprising the steps of:

placing first and second plates into the incision;

connecting the first and second plates to each other;

holding the first and second plates together in a predetermined relationship with a passageway defined therebetween for receiving a cannula;

after the steps of connecting and holding the first and second plates together, placing a ring on the tissue so that the ring surrounds the incision; and drawing the plates toward diametrically opposite locations on the ring to thereby enlarge the diameter of the incision.

20. A method of enlarging an incision in a tissue, said method comprising the steps of:

placing a ring on the tissue so that the ring surrounds the incision;

placing first and second plates into the incision;

connecting the first and second plates to each other and holding the first and second plates together in a predetermined relationship with a tubular passageway having a substantially constant diameter defined therebetween for guidingly receiving a cannula;

placing a guide plate on at least one of the first and second plates and using the guide plate to direct the first and second plates through an incision; and drawing the plates towards diametrically opposite locations on the ring to thereby enlarge the diameter of the incision.

21. A method of enlarging an incision in a tissue, said method comprising the steps of:

placing a ring on the tissue so that the ring surrounds the incision;

placing first and second plates into the incision;

connecting said first and second plates to each other and holding the first and second plates together in a predetermined relationship by surrounding the first and second plates with a cap to hold the first and second plates together in assembled relationship in which a cannula passageway is defined between the first and second plates; and drawing the plates towards diametrically opposite locations on the ring to thereby enlarge the diameter of the incision.

22. The method according to claim 21 including the step of placing a cannula in the passageway between the first and second plates and altering the relative positions of the first and second plates through the cap to accommodate the cannula.

23. A method of enlarging such a tissue, said method comprising the steps of:

placing a ring on the tissue so that the ring surrounds the incision;

placing first and second plates into the incision;

connecting the first and second plates to each other and holding the first and second plates together in a predetermined relationship with a passageway defined therebetween for receiving a cannula;

drawing the plates towards diametrically opposite locations on the ring to thereby enlarge the diameter of the incision; and removing the first and second plates and replacing the first and second plates with first and second retractor elements.

24. A method of enlarging an incision in a tissue, said method comprising the steps of:

defining an incision in the tissue;

placing a ring on the tissue so that the ring surrounds the incision;

placing first and second plates into the incision;

directing a cannula with a shoulder thereon into the incision;

captively holding the tissue between the first and second plates and the cannula shoulder;

connecting the first and second plates to each other and holding the first and second plates together in a predetermined relationship to define a tubular passageway having a substantially constant diameter defined therebetween for guidingly receiving a cannula; and drawing the plates toward diametrically opposite locations on the ring to thereby enlarge the diameter of the incision.

25. The method according to claim 24 wherein the shoulder is defined by an inflatable membrane that can be placed selectively in a collapsed and an expanded state and including the step of inflating the membrane after the cannula is directed through the incision.

26. A method of performing surgery comprising the steps of:

directing a cannula through an incision in tissue so that the cannula extends into a cavity in which surgery is to be performed;

performing a laproscopic procedure;

placing a converter unit on the cannula;

using the converter unit to enlarge the incision sufficiently to remove objects from the cavity;

removing the converter until from the cannula; and attaching retractor elements to the tissue to hold the enlarged incision open.

27. The method of performing surgery according to claim 26 including the step of performing one of a laparoscopic and microsurgical procedure in the cavity and removing an object from the body cavity through the enlarged incision.

28. The method of performing surgery according to claim 26 including the step of holding the cannula in an operative position relative to the tissue.

* * * * *